(12) United States Patent
Lehtoluoto

(10) Patent No.: US 6,694,183 B1
(45) Date of Patent: Feb. 17, 2004

(54) SKIN CLEANSING DEVICE

(76) Inventor: Eeva-Liisa Lehtoluoto, Kauppapuistikko 35, FIN-65100 Vaasa (FI)

( * ) Notice: Subject to any disclaimer, the term of this patent is extended or adjusted under 35 U.S.C. 154(b) by 59 days.

(21) Appl. No.: 10/018,801
(22) PCT Filed: Jun. 20, 2000
(86) PCT No.: PCT/FI00/00549
§ 371 (c)(1), (2), (4) Date: Dec. 21, 2001
(87) PCT Pub. No.: WO00/78388
PCT Pub. Date: Dec. 28, 2000

(30) Foreign Application Priority Data

Jun. 21, 1999 (FI) .................................... 991409

(51) Int. Cl.[7] .............................. A61N 1/30; A61N 1/06
(52) U.S. Cl. ......................................... 604/20; 607/140
(58) Field of Search .................... 604/19, 20; 607/3, 607/152, 153, 139, 140, 141; 606/32, 41

(56) References Cited

U.S. PATENT DOCUMENTS 5,443,441 A    8/1995  De Claviere

FOREIGN PATENT DOCUMENTS

| EP | 0 225 556 | 6/1987 |
|----|-----------|--------|
| EP | 0 293 893 | 12/1988 |
| EP | 0 317 451 | 5/1989 |
| EP | 0 470 338 | 2/1992 |
| FR | 2 502 015 | 9/1982 |
| FR | 2 636 241 | 3/1990 |
| WO | 88/00846 | 2/1988 |
| WO | 90/06153 | 6/1990 |
| WO | 91/16944 | 11/1991 |
| WO | 98/29158 | 7/1998 |

Primary Examiner—Sharon Kennedy
(74) Attorney, Agent, or Firm—Young & Thompson

(57) ABSTRACT

A skin cleansing device for cleansing facial skin includes electrode pairs attached to a facial mask and a cleansing signal generator for generating an alternating electric cleansing signal, the electrode pairs being operatively connected to the signal generator to apply the cleansing signal to charged molecules of the cleansing solution located at mask absorbent areas to create alternate backward and forward motion of the facial skin surface.

20 Claims, 2 Drawing Sheets

SKIN CLEANSING DEVICE

FIELD OF THE INVENTION

The invention relates to a skin cleansing device for cleansing facial skin in particular, the skin cleansing device comprising a facial mask, two or more electrodes to be attached to the facial mask, a cleansing signal generator for generating an electric cleansing signal, and means for conveying the cleansing signal from the cleansing signal generator to the electrodes.

BACKGROUND OF THE INVENTION

Cleansing methods mainly of three different types are nowadays used for cleansing human facial skin. The first method is based on utilizing different cleansing solutions and cleansing creams. In the method, cleansing solution absorbed in a piece of cotton, for example, is brought into contact with the skin in order to wipe the skin and dissolve impurities from the surface thereof. If the cleansing solution is to be left on the skin for a longer time to provide deeper cleansing and a more effective cleansing effect, the cleaner can be made more solid by combining it with a thicker cream or gel.

The second method is called exfoliation and it is based on using so-called exfoliating agents. In this method, a cleanser containing an abrasive material to mechanically rub the surface of the skin is spread on the skin. Exfoliation mechanically removes cell layers from the surface of the skin but leaves layers located deeper in the skin uncleansed.

The third method is based on utilizing the cooperative effect of a dissolving cleansing solution and electric current as the cleansing method. A cleansing solution is then used wherein the effective agents are electrically charged molecules, or ions. By bringing electric current into contact with the cleansing solution spread on the skin, the ions are made to move and transfer molecules of the cleanser into the skin, and, on the other hand, to transfer away from the pores impunties dissolved from the skin by the cleansing solution and to be removed therefrom. Hence, the skin purifying effect of the cleansing method can be improved and the deeper layers of the skin purified. The electric current is generated by a cleansing signal generator developed for the purpose, and it is conveyed to the skin by electrodes arranged in connection with a treatment towel or the like absorbing the cleansing solution and being preferably shaped according to the contours of an area in the skin to be treated.

Devices are previously known wherein pharmaceuticals or other conditioning agents are transferred into the body through the skin based on electrically charged molecules of the pharmaceuticals or conditioning agents and electric current. For example, U.S. Pat. No. 5,443,441 describes such a device. The purpose of the device is to transfer cosmetic conditioning agents into the skin by utilizing electric current. Also other devices are known that operate on a similar principle. In these devices, the current used for the treatment is usually direct current since the active agent is to be transferred in one direction only. Furthermore, devices are previously known wherein electric current or electric voltage is used in activating and rehabilitating muscles.

It can be generally stated, however, that the known devices and methods usually focus on transferring pharmaceuticals and cosmetic agents through the skin, activating muscles, improving the appearance or condition of the skin or tissues under the skin using at least partly mechanical means, even though these devices use electric current to generate a mechanical motion. The known devices are characterized in that they are developed to be used by professionals and experts in the field, which means that in order to achieve a favourable response and adequate user and patient safety, the users must have a proper knowledge of the treatment method used and the operation of the device; therefore, the devices are not suitable for non-professional use.

The known devices utilizing electric current usually use at least two electrodes, at least one electrode being attached to the body at a relatively long distance from the area of the skin to be treated. This means that in the body the electric current travels the distance between the electrodes, and, if alternating current is used, a risk exists that the alternating current travelling in the body might cause a serious heart dysfunction. When devices and methods based on direct current are used, the negative electrode is attached to a given point in the body, in which case the current travels via the same area in the skin throughout the entire treatment process. At said point, the relative current density may become high and the time of exposure long, which may cause hypersensitivity reactions to both electricity and manufacturing materials of the electrodes particularly at the points where the electrodes come into contact with the skin.

Since the known devices are intended for professionals, an average domestic user may often find them too expensive.

BRIEF DESCRIPTION OF THE INVENTION

An object of the present invention is to implement a skin cleansing device so as to alleviate the above-mentioned problems and to provide a simple, easy-to-use, safe and inexpensive device particularly for skin cleansing for domestic use. This is achieved by a skin cleansing device disclosed in the preamble, the skin cleansing device being characterized in that the electrodes to be attached to the facial mask are arranged as electrode pairs comprising the positive electrode and the negative electrode, all electrode pairs are located in the facial mask substantially in the facial area, and the cleansing signal generated by the cleansing signal generator is an alternating current signal having substantially the shape of a square wave.

Preferred embodiments of the invention are disclosed in the dependent claims.

The idea underlying the invention is that by arranging the electrodes to be attached to the facial mask as electrode pairs comprising the positive electrode and the negative electrode and by placing all electrode pairs in the facial mask substantially in the facial area, several advantages improving the cleansing efficiency, user-friendliness and safety of the skin cleansing device are achieved.

When all electrodes are located in the area of the skin to be cleansed and when they are placed in the facial mask, the user is provided with a simple and easy-to-use mask structure which can be held in place throughout the entire cleansing process. In addition, as all electrodes are located in the area of the skin to be cleansed, the electric cleansing signal used by the cleansing device only affects in the area of the skin to be cleansed, which has the advantage that the electric current travels in the body only in the area to be cleansed. Hence, the signal does not have to travel a long distance in the body, so it is unable to stress or harm the action of other tissues or the heart. Neither can the electric signal then cause a hypersensitivity reaction, thus improving the safety of the device as a treatment device.

Arranging the electrodes as electrode pairs has the advantage that the electrodes can be formed so as to have a preferred size and shape in regard to the area of the skin to be treated. For example, in the area of the forehead and the chin, the electrodes have a different preferred size and shape. A further advantage is that the active cleansing signal in the area of an electrode pair remains regional, thus improving the cleansing efficiency.

In a skin cleansing device of the invention, a cleansing signal which is generated by a cleansing signal generator and which is an alternating voltage signal having the shape of a square wave is used to provide an electric cleansing effect, i.e. to make the ions in the cleansing solution move. The ions in the cleansing solution are then engaged in an alternate backward and forward motion, which has the advantage that by the positive current impulse, positive ions of the cleansing solution are transferred deeper in the skin through the surface of the skin, while by the negative current impulse, correspondingly, the positive ions are transferred from the skin or vice versa, depending on the charge of the ion. Hence, the cleansing effect is enhanced since the device both transfers the cleansing solution to the skin and transfers impurities dissolved by the cleansing device from the skin. In skin cleansing, a preferred cleansing effect to yield adequate penetrability into the pores is achieved at a frequency of about 2000 Hz. A further advantage of this frequency is that it is sufficiently high so as not to harm the action of the heart.

In the skin cleansing device of the invention, the signal generated by the cleansing signal generator is substantially of the shape of a square wave. An advantage of the square wave is its high efficiency. The time taken by the skin cleansing process per a cleansing session can then be kept short. Furthermore, it has been found out that the third and the fifth harmonic wave in the square wave produce preferred cleansing effects. The voltage of the signal generated by the cleansing signal generator is lower than 5 V. A voltage of this magnitude is sufficiently low to be safe, producing, however, an adequate skin cleansing efficiency.

The facial mask of the skin cleansing device of the invention has a sandwich construction. A layer to be arranged against the face is manufactured of a substantially absorbent material with high receptivity of the cleansing solution, such as terry cloth, paper or some such material with high absorbency or a combination thereof. For a good cleansing efficiency, it is important that the material of the facial mask is capable of receiving a sufficient amount of the skin cleansing solution, and, in addition, feels comfortable against the face. Electrodes having a conductive contact with the cleansing solution are connected to a layer to be arranged on top of the absorbent layer, which can be manufactured of dense cloth, for example. A layer manufactured of a substantially more rigid material, such as plastic, serves as the outer surface layer of the mask. An advantage of this solution is that the facial mask is strong and easy to clean, and it enables the use of disposable components as the layer receiving the cleansing solution, for example.

In an implementation according to an embodiment of said skin cleansing device, the electrodes are manufactured of substantially chloridized silver. As a noble metal, silver is safe, causing no hypersensitivity reactions on the skin. Chloridized, a silver electrode has excellent electrical conductivity when used particularly as electrodes.

The skin cleansing device of the invention operates on low voltage direct current. Hence, being particularly designed for domestic skin cleansing use, an advantage of the skin cleansing device of the invention is its safety.

BRIEF DESCRIPTION OF THE DRAWINGS

The invention is now described in closer detail in connection with the preferred embodiments of the invention and with reference to the accompanying drawings, in which.

DETAILED DESCRIPTION OF THE INVENTION

Figure 1:
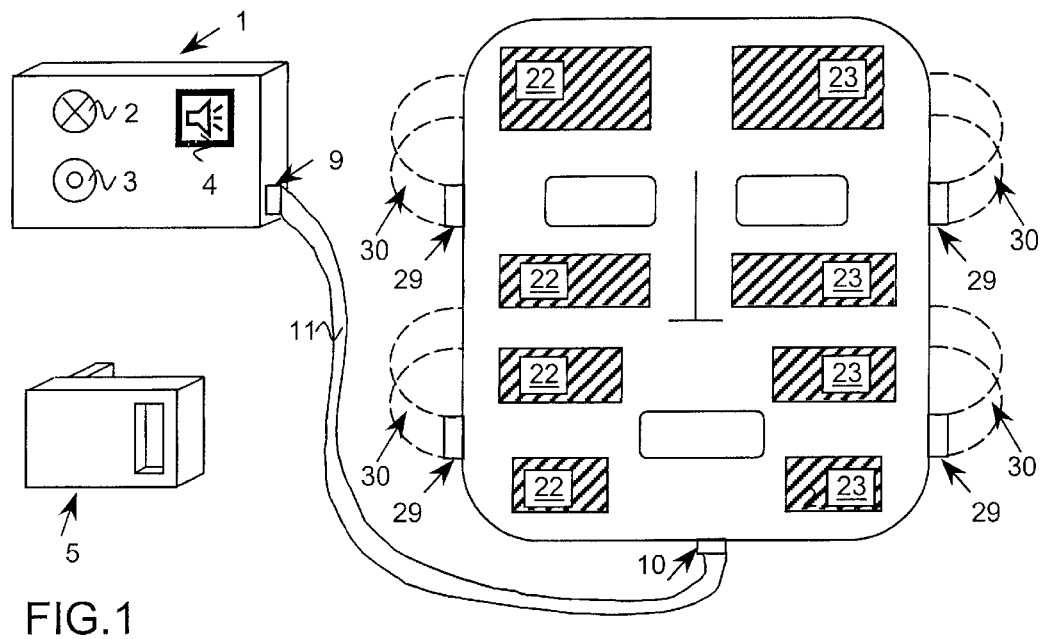
FIG. 1 shows components in a skin cleansing device of the invention.

FIG. 1 shows a preferred embodiment of a skin cleansing device of the invention. The figure shows separate components in the device, the components including a facial mask 21, a cleaning signal generator 1, and means (conductors 11 and connectors 9, 10 thereof) for conveying a cleansing signal 18 from the cleaning signal generator 1 to the facial mask 21. The device further comprises a charger 5 for charging a battery 7 of the cleaning signal generator 1.

Figure 2:
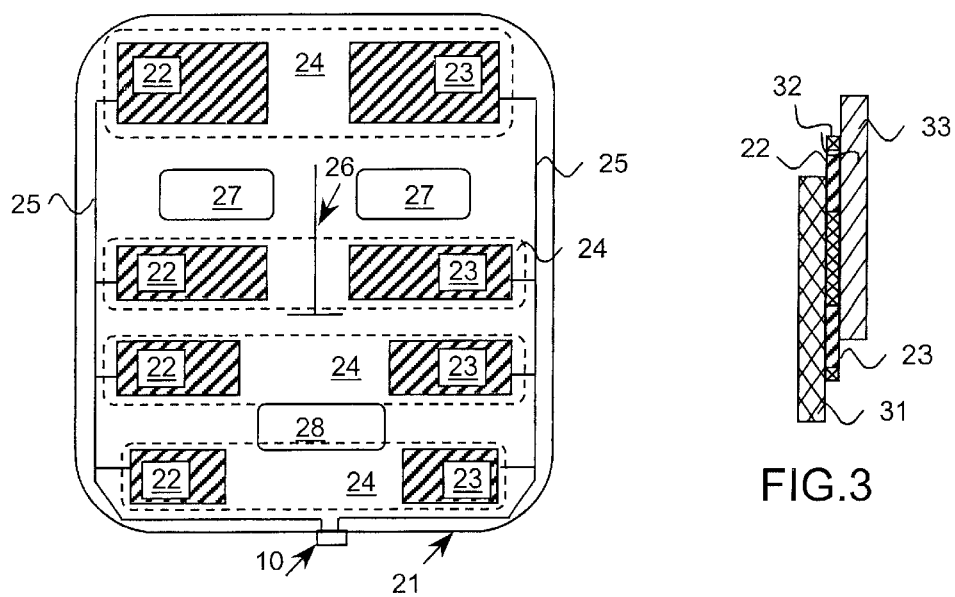
FIG. 2 shows how electrodes are located in a facial mask of the skin cleansing device according to a preferred embodiment of the invention as seen from the front of the facial mask.

FIG. 2 shows, as seen from the front of the facial mask, the shape of the facial mask 21 of the skin cleansing device of the invention and a schematic disposition of electrodes 22, 23 as electrode pairs 24. A characterizing feature of the invention is the disposition of the electrodes 22, 23 as the electrode pairs 24. One electrode pair 24 comprises two electrodes 22, 24, the first one of the, electrodes being the positive electrode 22 and the second being the negative electrode 23. The electrodes 22, 23 forming the electrode pair 24 are placed within the same facial area such that the positive electrode 22 and the negative electrode 23 of the electrode pair 24 are located at the opposite sides of the face, an electrode pair being located on the forehead and another on the chin, for example. The electrodes 22, 23 of different electrode pairs 24 differ in size and shape at different points of the face. All electrodes 22, 23 in the facial mask 21 are located within the facial area. The facial mask also comprises connectors 10, through which the electrodes 22, 23 are connected to the conductors 11 connected to the cleansing signal generator 21. Fasteners 29 to which a band 30, for example, can be attached are provided on both sides of the facial mask 21, whereby the facial mask 21 can be tightened over the face during the cleansing process.

Figure 3:
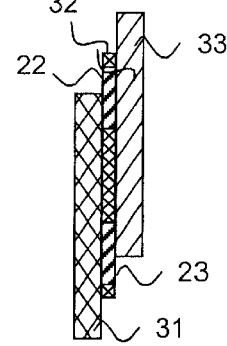
FIG. 3 is a cross-sectional top view of the structure of the facial mask according to FIG. 2.

FIG. 3 is a cross-sectional top view of the structure of the facial mask 21. The facial mask 21 comprises different layers. It is preferable to construct the facial mask 21 from, for example, the following layers comprising different materials. A layer 31 to be arranged against the face comprises a cleansing towel, which is made of an absorbent material and which is able to absorb a sufficient amount of a cleansing solution as far as the efficiency of the cleansing process is concerned. The absorbent material is, for example, preferably terry cloth, a cellulose-based material suitable for the purpose, such as paper, or another such material with high absorbency. The layer 31 of the facial mask 21 to be arranged against the face is detachable. Detached from the facial mask 21, the layer 31 can thus be cleaned separately, or disposable cleansing towels can be used.

On top of the absorbent layer 31 is provided a layer 32, the electrodes 22, 23 connected thereto. The layer 32 is made of dense cloth, for example. Essential parts of the electrodes 22, 23 can preferably be manufactured of chloridized silver. The electrodes 22, 23 are preferably attached to the cloth by using, for example, a technique called screen printing, in which case an electrode pattern of a desired design is printed on the surface of the cloth, the electrodes 22, 23 in the electrode pattern comprising thin metal films, for example. An electrode structure is also feasible wherein the electrodes 22, 23 comprise a thin thread having the shape of the electrodes. The electrodes 22, 23 are connected by the conductors 25 to the connectors 10, which convey the cleansing signal 18 from the cleansing signal generator 1 to the electrodes 22, 23. An outer layer 33 made of a more rigid material serves as the topmost layer in the facial mask 21. The material of the outer surface layer 33 is mouldable such that the facial mask 21 can be shaped and bent according to the contours of a customers face to be treated so as to achieve as large an area to be cleansed as possible. The material is preferably mouldable plastic or the like. The facial mask 21 comprises openings for eyes 27, nose 26 and mouth 28.

The operation principle of the skin cleansing device of the invention is such that a cleansing solution, such as sodium carbonate is absorbed in the cleansing solution receiving part 31 of the facial mask 21 of the device, and the facial mask 21 is placed on the face to be cleansed. Next, the cleansing signal conductors 11 are connected to the connectors 10 arranged in the facial mask 21 and to the connectors 9 arranged in the cleansing signal generator 1, and the cleansing signal generator 1 is switched on by pressing the start button. The cleansing signal generator then starts supplying the cleansing signal 18 having the shape of a square wave to the electrodes 22, 23 located in the facial mask 21. The effective agents in the cleansing solution are electrically charged molecules, or ions. When the cleansing signal 18 generated by the cleansing signal generator 1 is conveyed to the cleansing solution spread on the skin, electric current makes the ions in the cleansing solution move back and forth and transfer the molecules in the cleansing solution to the pores in the deeper layers of the skin through the surface of the skin, and, on the other hand, transfer from the pores impurities dissolved by the cleansing solution and to be removed from the skin.

Figure 5:
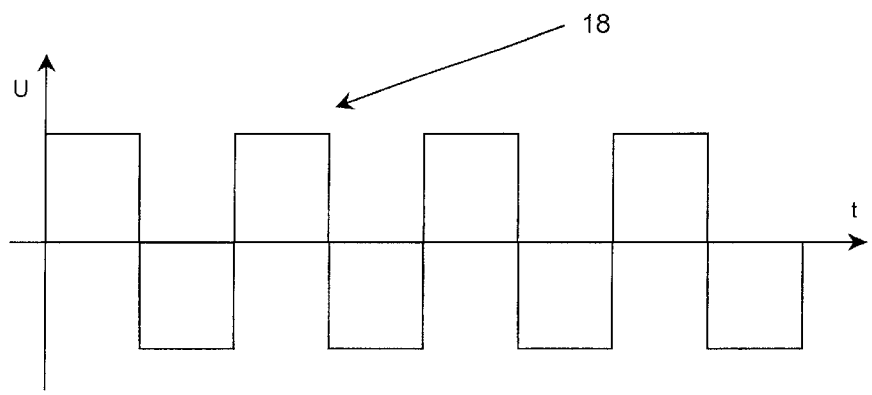
FIG. 5 shows the shape of a cleansing signal generated by the cleansing signal generator of the skin cleansing device of the invention.

FIG. 5 shows the cleansing signal 18 generated by the cleansing signal generator 1. In order to yield preferred penetrability into the pores, the alternating voltage signal having the shape of a square wave and generated by the cleansing signal generator 1 has a frequency of 2000 Hz. The voltage of the cleansing signal is lower than 5 V, which enables the current to travel between the electrodes 22, 23 of the facial mask 21, but which, however, does not endanger the action of the heart or other tissues in the body. If, in addition to the cleansing effect being provided, skin conditioning molecules are to be transferred into the skin in connection with the cleansing, a direct current component can also be attached to the cleansing signal 18. Hence, the device operates as a cleansing device for simultaneously transferring skin conditioning agents into the skin through the surface of the skin.

By a signal light 2 connected thereto, the cleansing signal generator 1 indicates that the device is in operation. The duration of the cleansing process is set to be constant, a preferred duration being ten minutes per a cleansing session.

The cleansing signal generator 1 indicates the end of a cleansing session by a voice signal given by a buzzer 4 connected thereto, and stops generating the cleansing signal 18 to the electrodes 22, 23. The cleansing process is initiated by pressing a start button 3.

The voltage necessary for the cleansing signal generator 1 is conveyed to the generator by the battery 7, which is charged in the separate charger 5. The battery 7 charged in the separate charger 5 improves the safety of the device and simplifies the structure thereof, since the supply voltage is thus prevented from being conveyed to the cleansing signal generator 1 under all circumstances.

Figure 4:
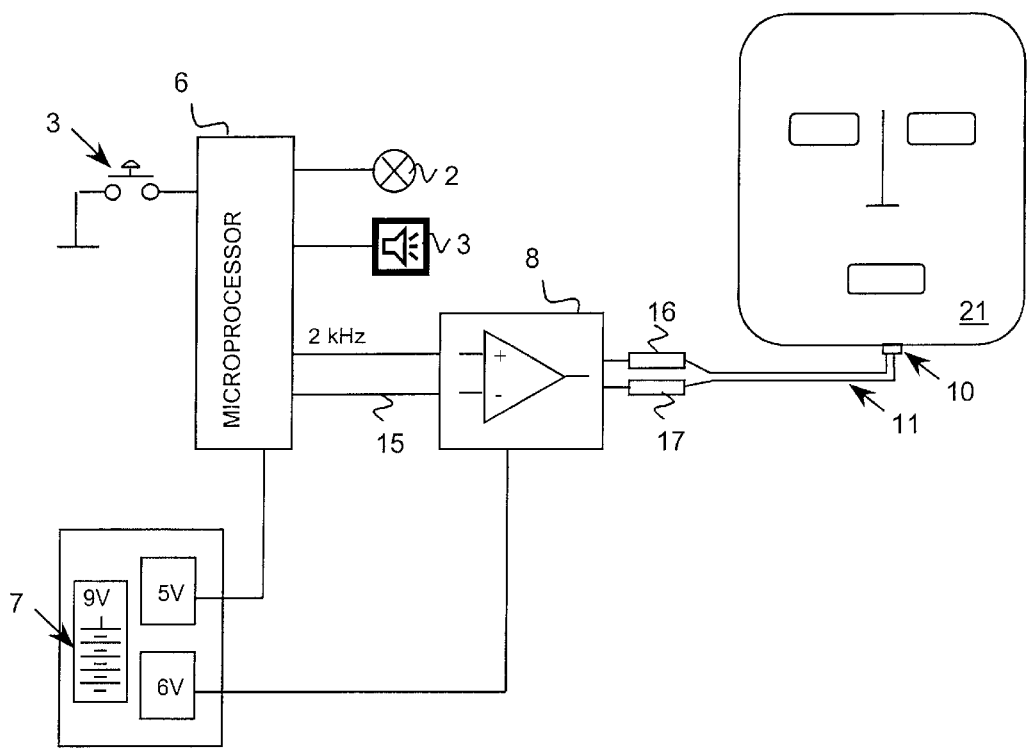
FIG. 4 is a block diagram of structural parts of a cleansing signal generator of the skin cleansing device of the invention.

FIG. 4 is a block diagram showing components necessary for generating the cleansing signal 18 of the cleansing signal generator 1. A central component of the cleansing signal generator 1 is a microprocessor 6, which serves to generate a 2000 Hz control signal to an output amplifier 8, start the cleansing signal generator 1 on the basis of pressing the start button 3 and automatically stop generating the cleansing signal 18 when the cleansing time is over, control the operation of the signal light 2 indicating the operation of the device, and control the operation of the buzzer 4 indicating the end of the cleansing time. Furthermore, the microprocessor 6 can be programmed to monitor the technical condition of the cleansing signal generator 1 of the device and the components connected thereto, and to report error situations by a voice signal given by the buzzer 4, for example.

The battery 7, which preferably has a voltage of 9 V and which produces the low voltage direct current necessary for the device, serves as a power source of the cleansing signal generator 1. The power source generates the operating voltage for the microprocessor 6, the buzzer 4, the signal light 2 and the output amplifier 8.

The cleansing signal 18 of the cleansing device is generated by the output amplifier step 8 formed by MOSFET transistors, for example. A 2000 Hz control signal 15 is supplied to the output amplifier step 8 from the microprocessor 6. The output amplifier step 8 forms the cleansing signal 18 by amplifying the control signal 15 to a voltage of about 5 V. From the output amplifier 8, the cleansing signal 18 is supplied to the electrodes 22, 23 in the facial mask 21 through terminal resistors 16, 17. The terminal resistors 16, 17 restrict the current supplied to the electrodes 22, 23 to a preferred level as far as the cleansing is concerned.

Although the invention has been described above by way of example with reference to one embodiment only, it is obvious that the invention is not restricted thereto but can be modified in many ways within the scope of the inventive idea disclosed in the attached claims.

What is claimed is:

1. A skin cleansing device for cleansing facial skin with a cleansing solution, the skin cleansing device comprising:
   a facial mask,
   two or more electrodes arranged as electrode pairs, comprising a positive electrode an a negative electrode, the electrodes being located in the facial mask substantially in the facial area,
   a cleansing signal generator for generating an electric cleansing signal, and
   means for conveying the cleansing signal from the cleansing signal generator to the electrodes,
   wherein, the cleansing signal generated by the cleansing signal generator is an alternating current signal accomplishing an alternating backward and forward motion through the surface of the skin of electrically charged molecules, or ions to be found in a cleansing solution absorbed in the facial mask.

2. A skin cleansing device as claimed in claim 1 wherein the alternating current signal has substantially the shape of a square wave.

3. A skin cleansing device as claimed in claim 2 wherein the voltage of the cleansing signal generated by the cleansing signal generator is lower than 5 V.

4. A skin cleansing device as claimed in claim 3 wherein the frequency of the cleansing signal generated by the cleansing signal generator is higher than or equal to 2000 Hz.

5. A skin cleansing device as claimed in claim 1 wherein the facial mask has a sandwich construction comprising at least an absorbent layer receiving a cleansing solution to be arranged against the face, a layer receiving the electrodes, and an outer surface layer manufactured from a substantially more rigid material.

6. A skin cleansing device as claimed in claim 5 wherein the absorbent layer receiving a cleansing solution to be arranged against the face is detachable.

7. A skin cleansing device as claimed in claim 1 wherein the electrodes are manufactured from at least substantially chloridized silver.

8. A skin cleansing device as claimed in claim 1 wherein the positive electrode and the negative electrode of the electrode pair are located substantially at different sides of the face.

9. A skin cleansing device as claimed in claim 1 wherein the electrodes in the electrode pair are of different sizes.

10. A skin cleansing device as claimed in claim 1 wherein the device operates on low voltage direct current.

11. A skin cleansing device as claimed in claim 10 wherein the electrodes are manufactured from at least substantially chloridized silver.

12. A skin cleansing device as claimed in claim 10 wherein the positive electrode and the negative electrode of the electrode pair are located substantially at different sides of the face.

13. A skin cleansing device as claimed in claim 10 wherein the cleansing signal is configured to acting on positive ions of the cleansing solution at the facial area and create alternating backward and forward motion at the surface of the facial skin.

14. A skin cleansing device for cleansing facial skin with a cleansing solution, the skin cleansing device comprising:

a facial mask with a facial area;

a pair of electrodes located the facial area of the facial mask;

a cleansing signal generator for generating an alternating electric cleansing signal of at least 2000 Hz; and means for conveying the cleansing signal from the cleansing signal generator to the electrodes and to the facial area, the cleansing signal acting on ions of the cleansing solution at the facial area and creating alternating backward and forward motion at the surface of the facial skin.

15. A skin cleansing device as claimed in claim 14 wherein the alternating current signal is a square wave.

16. A skin cleansing device as claimed in claim 15 wherein the voltage of the cleansing signal generated by the cleansing signal generator is lower than 5 V.

17. A skin cleansing device as claimed in claim 16 wherein the electrodes in the electrode pair are of different sizes.

18. A skin cleansing device as claimed in claim 14 wherein the facial mask has a sandwich construction comprising at least an absorbent layer receiving a cleansing solution to be arranged against the face, a layer receiving the electrodes, and an outer surface layer manufactured from a substantially more rigid material.

19. A skin cleansing device as claimed in claim 18 wherein the absorbent layer receiving a cleansing solution to be arranged against the face is detachable.

20. A skin cleansing device for cleansing facial skin with a cleansing solution, the skin cleansing device comprising:

a facial mask with cleansing solution absorbent area;

a cleansing signal generator for generating an alternating electric cleansing signal of at least 2000 Hz; and an electrode pair connected to the absorbent area and to the signal generator to apply the cleansing signal to charged molecules of the cleansing solution located at the absorbent area to create alternate backward and forward motion of the facial skin.

* * * * *